US010867695B2

(12) United States Patent
Neagle, III

(10) Patent No.: US 10,867,695 B2
(45) Date of Patent: *Dec. 15, 2020

(54) SYSTEM AND METHOD FOR COMPREHENSIVE HEALTH AND WELLNESS MOBILE MANAGEMENT

(71) Applicant: Pharmalto, LLC, Plano, TX (US)

(72) Inventor: Charles E. Neagle, III, Plano, TX (US)

(73) Assignee: Pharmalto, LLC, Plano, TX (US)

( * ) Notice: Subject to any disclaimer, the term of this patent is extended or adjusted under 35 U.S.C. 154(b) by 994 days.

This patent is subject to a terminal disclaimer.

(21) Appl. No.: 14/822,862

(22) Filed: Aug. 10, 2015

(65) Prior Publication Data

US 2015/0347689 A1 Dec. 3, 2015

Related U.S. Application Data

(63) Continuation-in-part of application No. 13/916,022, filed on Jun. 12, 2013, which is a continuation-in-part (Continued)

(51) Int. Cl.
*G16H 10/60* (2018.01)
*G06F 19/00* (2018.01)

(Continued)

(52) U.S. Cl.
CPC .......... *G16H 10/60* (2018.01); *A61B 5/0002* (2013.01); *A61B 5/0015* (2013.01);

(Continued)

(58) Field of Classification Search
CPC ........ G16H 10/60; G16H 40/63; G06F 19/00; G06F 19/3418; G06F 19/3475;

(Continued)

(56) References Cited

U.S. PATENT DOCUMENTS 5,963,136 A 10/1999 O'Brien
6,988,075 B1 1/2006 Hacker
(Continued)

OTHER PUBLICATIONS kickstarter.com. NODE: a modular, handheld powerhouse of sensors by George Yu—KickStarter, www.kicker.com/projects/108684420/node-a-modular-handheld-powerhouse-of-sensors, downloaded Nov. 27, 2015, 14 pages.

(Continued)

*Primary Examiner* — Linh Giang Le
(74) *Attorney, Agent, or Firm* — Wei Wei Jeang; Grable Martin Fulton PLLC

(57) ABSTRACT

A system for health and wellness mobile management comprises a database operable to store a health and wellness data record associated with a patient/data owner, a content management system adapted to strictly control access to the health and wellness data record stored in the database according to access rules set by the patient, a web interface adapted to interface with information requesters submitting requests for access to the health and wellness data record via a web application, an external connect interface adapted to interface with external systems and applications for receiving health and wellness data associated with the patient, a prescription interface adapted to receive a pharmaceutical prescription for the patient submitted by a healthcare provider, and a patient identification accessory adapted to uniquely identify the patient as the data owner of the health and wellness data record stored in the database. Other features include nutritional valuation and fitness challenges.

46 Claims, 10 Drawing Sheets

Related U.S. Application Data of application No. 13/908,179, filed on Jun. 3, 2013, now abandoned.

(60) Provisional application No. 61/655,315, filed on Jun. 4, 2012, provisional application No. 62/073,468, filed on Oct. 31, 2014.

(51) Int. Cl.
  *A61B 5/00*    (2006.01)
  *G16H 40/63*    (2018.01)
  *H04W 4/80*    (2018.01)
  *G06Q 50/24*    (2012.01)
  *A61B 5/083*    (2006.01)
  *A61B 5/0404*    (2006.01)
  *A61B 5/091*    (2006.01)
  *A61B 5/08*    (2006.01)

(52) U.S. Cl.
  CPC .......... *A61B 5/0404* (2013.01); *A61B 5/0836* (2013.01); *A61B 5/742* (2013.01); *G06F 19/322* (2013.01); *G06F 19/3418* (2013.01); *G06F 19/3456* (2013.01); *G06F 19/3475* (2013.01); *G06Q 50/24* (2013.01); *G16H 40/63* (2018.01); *H04W 4/80* (2018.02); *A61B 5/0004* (2013.01); *A61B 5/082* (2013.01); *A61B 5/091* (2013.01); *A61B 5/681* (2013.01)

(58) Field of Classification Search
  CPC .... G06F 19/3456; H04W 4/80; A61B 5/0836; A61B 5/0404; A61B 5/0015; A61B 5/117; A61B 5/742; A61B 5/0004; A61B 5/082; A61B 5/091; A61B 5/681; A61B 5/0002; G06Q 50/24
  See application file for complete search history.

(56) References Cited

U.S. PATENT DOCUMENTS

| | | | | |
|---|---|---|---|---|
| 7,949,545 | B1 * | 5/2011 | Madras | G06Q 40/08 705/3 |
| 8,032,397 | B2 | 10/2011 | Lawless | |
| 2002/0188473 | A1 | 12/2002 | Jackson | |
| 2003/0036923 | A1 * | 2/2003 | Waldon | G06F 19/3456 705/2 |
| 2003/0052787 | A1 * | 3/2003 | Zerhusen | A47B 23/046 340/573.1 |
| 2005/0081601 | A1 * | 4/2005 | Lawson | G01N 33/497 73/23.3 |
| 2005/0182661 | A1 * | 8/2005 | Allard | G06F 21/6245 705/3 |
| 2006/0136197 | A1 | 6/2006 | Oon | |
| 2008/0319798 | A1 * | 12/2008 | Kelley | G16H 10/65 705/3 |
| 2009/0322513 | A1 | 12/2009 | Hwang et al. | |
| 2010/0277274 | A1 * | 11/2010 | Toleti | G06F 21/32 340/5.7 |
| 2011/0001605 | A1 * | 1/2011 | Kiani | G06F 19/3418 340/5.6 |
| 2011/0202359 | A1 * | 8/2011 | Rak | G06F 19/324 705/1.1 |
| 2011/0224564 | A1 * | 9/2011 | Moon | A61B 5/00 600/509 |
| 2012/0179665 | A1 * | 7/2012 | Baarman | G06F 19/3475 707/709 |
| 2012/0209624 | A1 * | 8/2012 | Maitland | G06F 19/00 705/3 |
| 2013/0060096 | A1 | 3/2013 | Galli et al. | |

OTHER PUBLICATIONS microdaq.com, Carbon Monoxide (CO) Data Logger with USB Interface—EasyLog CO Data Recorder, www.mircrdaq.com/lascar/co_data_logger.php, downloaded Nov. 27, 2015, 2 pages.

Spirometer—The Smartphone Physical, www.smartphonephysical.or/spirometer.html., downloaded Nov. 27, 2015, 2 pages.

testbreath.com, Smoking Cessation Testing: offering non-invasive solutions for all your gas detection needs, including hydrogen breath monitors, carbon-monoxide testers a . . . , www.testbreath.com/smoking-cessation-testing.asp, downloaded Nov. 27, 2015, 1 page.

THOR Medical System—THOR Laboratories—THORMED R&D—WaveFront Spirometrt—WaveFront Flow Meter www. thormed.com/index.php?page=products&id=spiro4, downloaded Nov. 27, 2015, 3 pages.

Wikipedia, the free enclyclopedia—Breath carbon monoxide, en.wikipedia.org/wiki/Breath_carbon_monoxide, downloaded Nov. 27, 2015, 3 pages.

Wikipedia, the free encyclopedia—Spirometer, en.wikipedia.org/wiki/Spirometer, downloaded Nov. 27, 2015, 5 pages.

\* cited by examiner

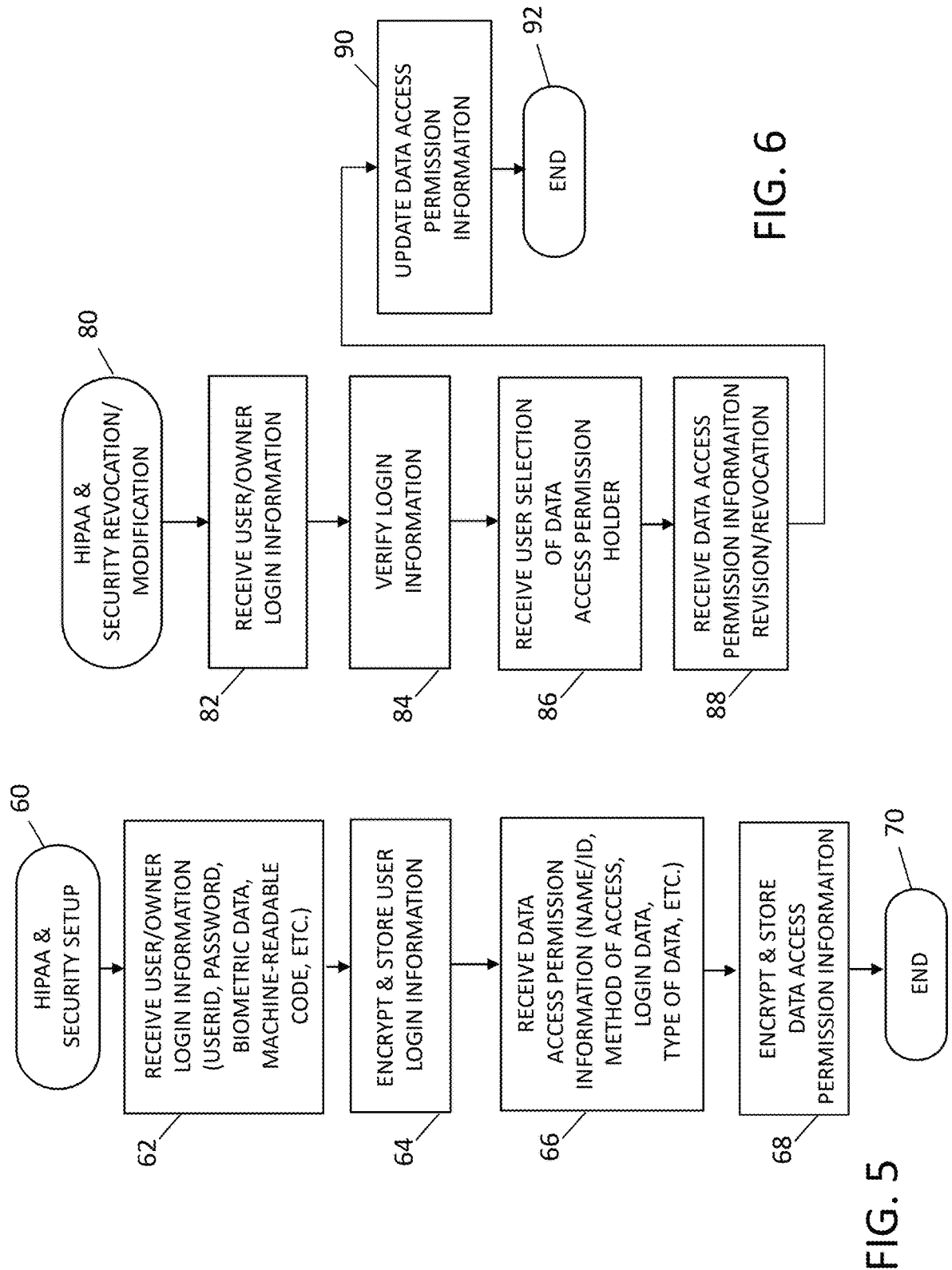

SYSTEM AND METHOD FOR COMPREHENSIVE HEALTH AND WELLNESS MOBILE MANAGEMENT

RELATED APPLICATION

This application is a continuation-in-part application of U.S. Non-Provisional application Ser. No. 13/916,022 filed on Jun. 12, 2013, which in turn is a continuation-in-part application of U.S. Non-Provisional application Ser. No. 13/908,179 filed on Jun. 3, 2013, which claims the benefit of U.S. Provisional Patent Application No. 61/655,315 filed on Jun. 4, 2014. This application further claims the benefit of U.S. Provisional Patent Application No. 62/073,468 filed on Oct. 31, 2014, entitled System and Method for Personalized Diet and Exercise Monitoring and Education. All aforementioned patent applications are incorporated herein by reference.

FIELD

The present disclosure relates the field of healthcare management, and more particularly to a system and method for comprehensive health and wellness mobile management.

BACKGROUND

In the 21st century, the Internet and the World Wide Web have become an increasingly important component of all types of communications. Internet penetration in North America is over 78%, and there are over 2.4 billion Internet users worldwide. In other words, a third of the world's population are Internet users. People are spending more and more time online, surfing the web, watching videos, uploading photographs, looking up information, and socializing on social networking sites. Along with the availability of web-enabled computing devices like the mobile telephone (formerly called smart telephones or personal digital assistants or PDAs), gaming devices, tablet computers, laptop computers, desktop computers, etc., the Internet is more accessible than ever before.

In 2008, people in the United States spent $234 billion on prescription medicine. Over $4.5 billion is spent annually on errors in the administration of medicines, or on unintended interactions and insurance or Medicare/Medicaid fraud and abuse. This nearly $5 billion is dwarfed by the estimate published by the New England Health Care Institute of $290 billion in annual costs associated with non-compliance, under-treatment, and non-treatment of diseases in the United States. With rising costs in healthcare, solutions are sought to control or reduce health-related expenses while improving patient care.

BRIEF DESCRIPTION OF THE DRAWINGS

FIG. 5 is a simplified flowchart illustrating a method of HIPAA and security setup process according to an exemplary embodiment of the present disclosure;

FIG. 6 is a simplified flowchart illustrating a method of HIPAA and security revocation/modification process according to an exemplary embodiment of the present disclosure;

DETAILED DESCRIPTION

Figure 1:
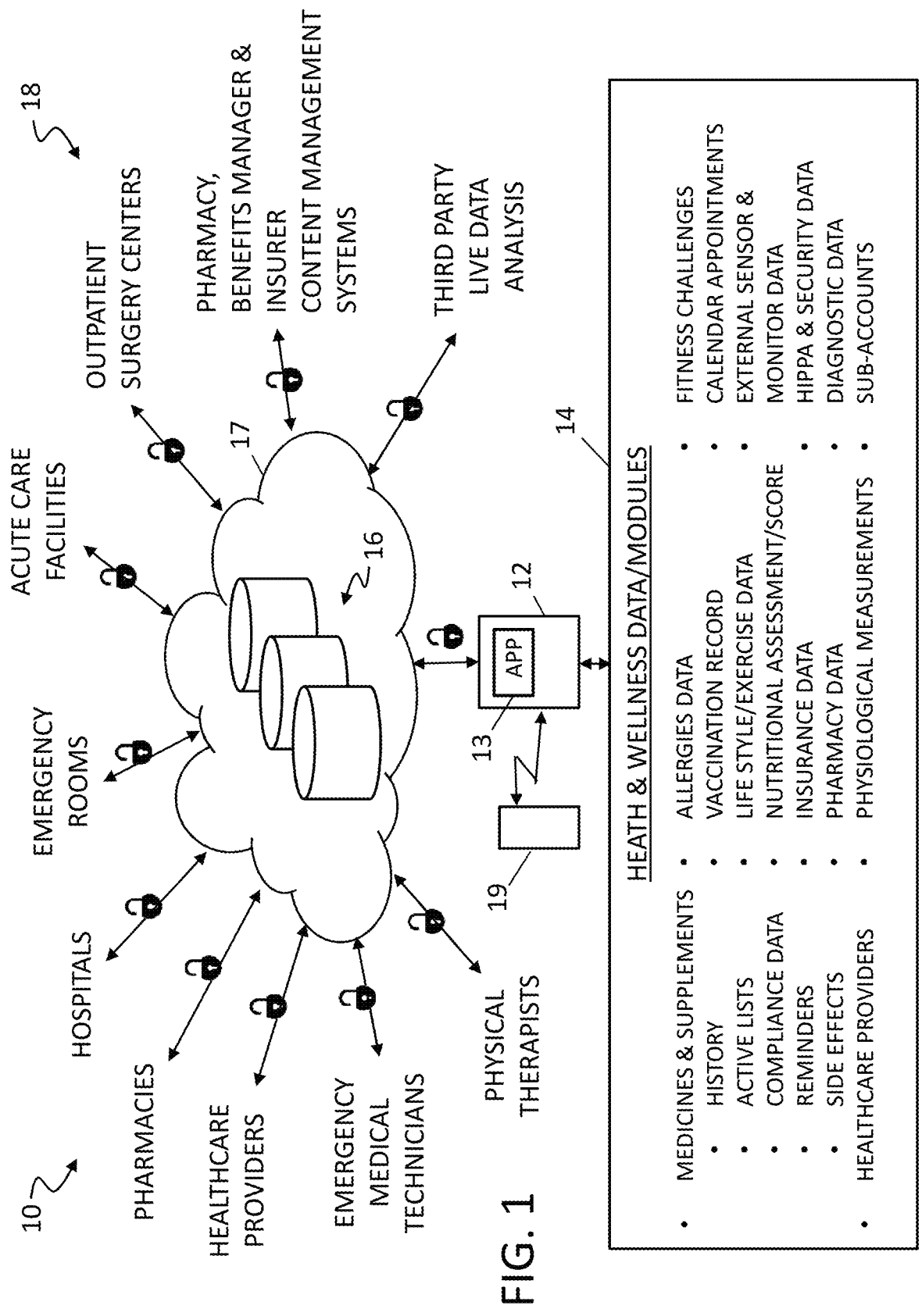
FIG. 1 is a simplified diagram illustrating a health and wellness mobile management system and method according to an exemplary embodiment of the present disclosure.

FIG. 1 is a simplified diagram illustrating a health and wellness mobile management system and method 10 according to an exemplary embodiment of the present disclosure. The system 10 is patient-centric resource that puts the patient's comprehensive and up-to-date health and wellness data easily within reach of the patient, such as via a software application or app 13 executing on a computing device 12 such as a mobile telephone, tablet computer, laptop computer, desktop computer, or other suitable computing devices in existence now or developed later. The health and wellness data belong to the patient or a legal guardian of the patient, rather than any physician, healthcare provider, institution, or corporation. The ownership of an account and the data may be transferred to another individual. For example, a dependent account and health and wellness data associated with a minor may be owned by a legal guardian or parent and associated with his/her account, but when the child reaches 18 years old, the account and health and wellness data ownership may be automatically transferred or can be directed to ensure proper ownership of the health and wellness data. Further, the patient has control to give others permission or authorization to access all or a subset of this data, and the patient has the sole authorization to terminate access to the data. For example, the patient may grant access to his data to his primary care physician, but terminate access by a surgeon that previously performed an operation on the patient, in addition to terminating access by the staff of the hospital at which the patient stayed for recuperation post-surgery.

This notion that a patient maintains sole control over his/her own health and wellness data rather than a healthcare provider, healthcare organization, health plan, pharmacy, or any third party is distinguished over the common convention of a patient's data being in the control of his/her physician, his hospital, and his pharmacy, and stored in disparate databases of his physician's, hospital's, and pharmacy's choosing, for example. The push has been to make the data portable from one healthcare provider to the next. However, the health and wellness mobility system and method described herein achieves true "portability" by creating a comprehensive collection of health and wellness data stored in a database that the patient has full control over, instead of the conventional setup in which the healthcare provider provide the patient his own data stored in a database that the healthcare provider has exclusive control and ownership rights. If the patient changes healthcare providers, the patient can simply terminate access by the old healthcare provider, and provide secured access to the new healthcare provider. Alternatively, the patient may choose to still allow the prior healthcare provider access so that she may provide secondary consultation on certain conditions.

A further advantage of the patient having full control over his/her own health and wellness data is that the patient may enter data and update the data whenever necessary. This is very different from the conventional system where the patient's data is updated only by the physician and pharmacy, and only when the patient visits the physician and/or pharmacy. As a result, the patient's health and wellness data is the most updated and current as they can be. Accordingly, even in an unexpected emergency situation, the most current health and wellness data are available to the healthcare personnel who are treating the patient.

The patient comprehensive health and wellness data 14 include information relating to medicines and supplements, such as medical history, active medicines, compliance data, reminders, ineffective medicine, and side effects. The patient health and wellness data 14 also include information about the healthcare providers, pharmacies, dependent sub-accounts, allergies, vaccination record, lifestyle and exercise data, dietary data, laboratory data, imaging data, medical charts, past, current (including automatically monitored) and future health/physiological parameters (heart rate, blood pressure, body temperature, perspiration, glucose level, blood oxygen level, risky addiction or behavior such as smoking cessation monitoring), diagnostics, HIPAA and security, legal document data (living will, do not resuscitate directives, power of attorney, etc.), and insurance data. These data are stored in one or more databases 16 such as in cloud data stores or cloud databases and accessible via the Internet by a variety of devices including computers, laptops, tablet computers, mobile telephones, etc.

These comprehensive health and wellness data may originate from a wide variety of sources 18, including, in no particular order, physical therapists, emergency medical technicians, healthcare providers, pharmacies, hospitals, emergency rooms, acute care facilities, laboratories, outpatient surgery centers, dieticians, benefits manager and insurer content management systems, and third party live data analysis systems. Further, the patient may wear monitoring devices that automatically measure and wireless transmit physiological parameters. Additionally, the patient may enter data or import data from other sources. The above are examples provided for illustrative purposes and other types of data related to the patient's health and wellness may be incorporated.

The health and wellness mobile management system and method 10 further uses various techniques to encourage compliance and behavioral modification for the benefits of better health and wellness. Behavioral modification techniques are employed to encourage the development of a particular beneficial behavior, the strengthening or the maintenance of existing healthful behaviors. The system employs positive reinforcement with the report of compliance data, set personal challenges (goal directed behavior) and can monitor the positive effect of compliance (the behavior we are attempting to instill) on a health measurement (blood pressure). Negative reinforcement when poor compliance results in the worsening of a health measurement. The avoidance principle is utilized by the ability for a health provider to intervene to correct a negative behavior (people do not like to be told they are not following directions). Peer pressure can also be recruited to change behavior or motivate to complete a goal through social network connections and group challenges.

Figure 2:
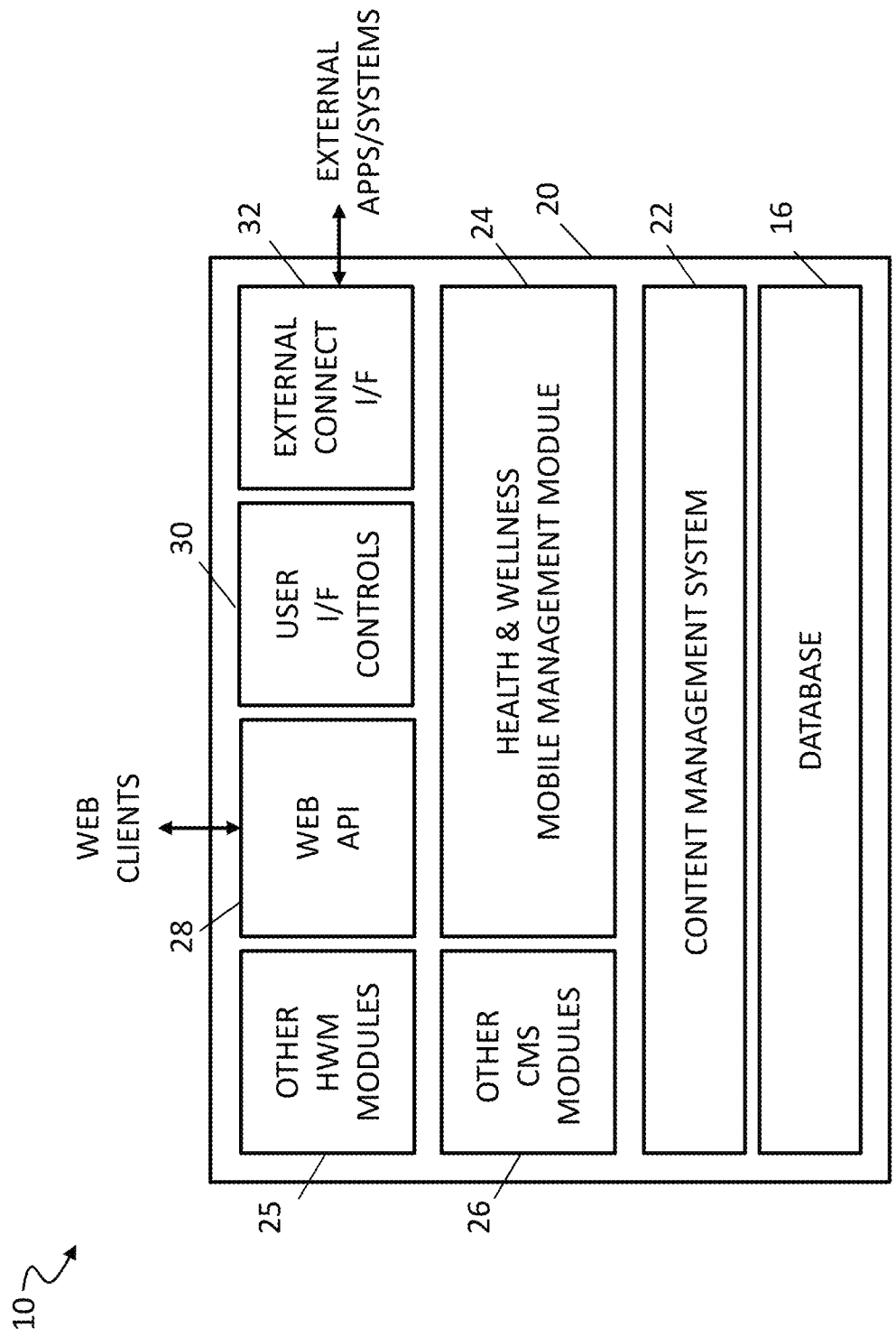
FIG. 2 is a simplified block diagram of the health and wellness mobile management system and method according to an exemplary embodiment of the present disclosure.

FIG. 2 is a simplified block diagram of the comprehensive health and wellness mobile management system and method 10 according to an exemplary embodiment of the present disclosure. The exemplary architecture of the health and wellness mobile management system and method 10 comprises a content management system (CMS) 22 that is generally a computer program that allows publishing, editing, and modifying content stored in the database 16. Preferably, all of a patient's data is wholly contained in a single record, where the access to each field of the record can be controlled. The data may be stored in XML or another suitable format. The content management system 22 enables additions of modules or plugins 24 and 26 that extend its functionality, and the content in the database 16 can be edited, published, deleted, and otherwise acted upon by any of the installed modules.

One such module is the health and wellness mobile management (WMM) module 24 that provides the primary functions of the system, such as user and role management, medication management, insurance provider policy and information, patient profile data, and supplement information. Other WMM modules 25 may be employed to provide time-zone sensitive notification and reminder functions for calendar appointments, taking medication and supplements, medication pick-up and refills, and notifications to healthcare professionals when certain health parameter thresholds have been exceeded (e.g., the blood pressure is over a certain limit set by the healthcare professional), for example. On the other hand, compliance and engagement may elicit positive messaging and encouragement from the system. For example, when medication is taken on time, or if weight/BMI remains consistent. The system may issue a warning message if certain restraints are violated. For example, a warning may be given (e.g., displayed, audio message, text message, etc.) if a medication reminder is within 30 minutes of a supplement reminder. The health parameter thresholds may be set by a healthcare provider for a particular patient, or set generally for all patients with a certain condition, for example. Using the general population threshold setting, a healthcare provider may screen a population for certain medical conditions such as high blood pressure. The patient/data owner may be encouraged to take certain measures, such as take his/her own blood pressure once a day, for example. Behavioral modification techniques may be employed to encourage the patient to self-monitor. The healthcare provider may choose to not receive any notification, or receive notification only when certain thresholds are exceeded.

Additionally, other CMS modules 26 that may be loaded and executed provide additional functionality, such as modules that provide animation on the website, control backend processes like email, user accounts, billing, etc. The health and wellness mobile management module 24, once loaded and executed by the content management system 22, may load additional modules for execution, such as a web API (application programming interface) 28, user interface controls module 30, and external connect interface module 32, for example.

The web API 28 provides a web-based interface to a plurality of web clients such as web browsers and a web mobile management app. The web API 28 may include or provide access to the health and wellness mobile management system website (which may include a separate mobile web site) and services that are operable to interface with web clients for various operating system and platforms, such as Android, Apple iPhone, Windows, etc. The user interface controls module 30 provide additional user interface control and functionality. The external connect interface module 32 provides an interface to external applications and systems that provide, additional health and wellness related functionality, for example, aerobic training, exercise coaching, walking logs, dieting logs, and wearable personal healthcare products like blood pressure cuffs, etc.

It should be noted that although the exemplary architecture of the system 10 described above incorporates a CMS, other suitable forms of applications or implementations that permit secured and selected access to published content may be used herein.

Figure 3:
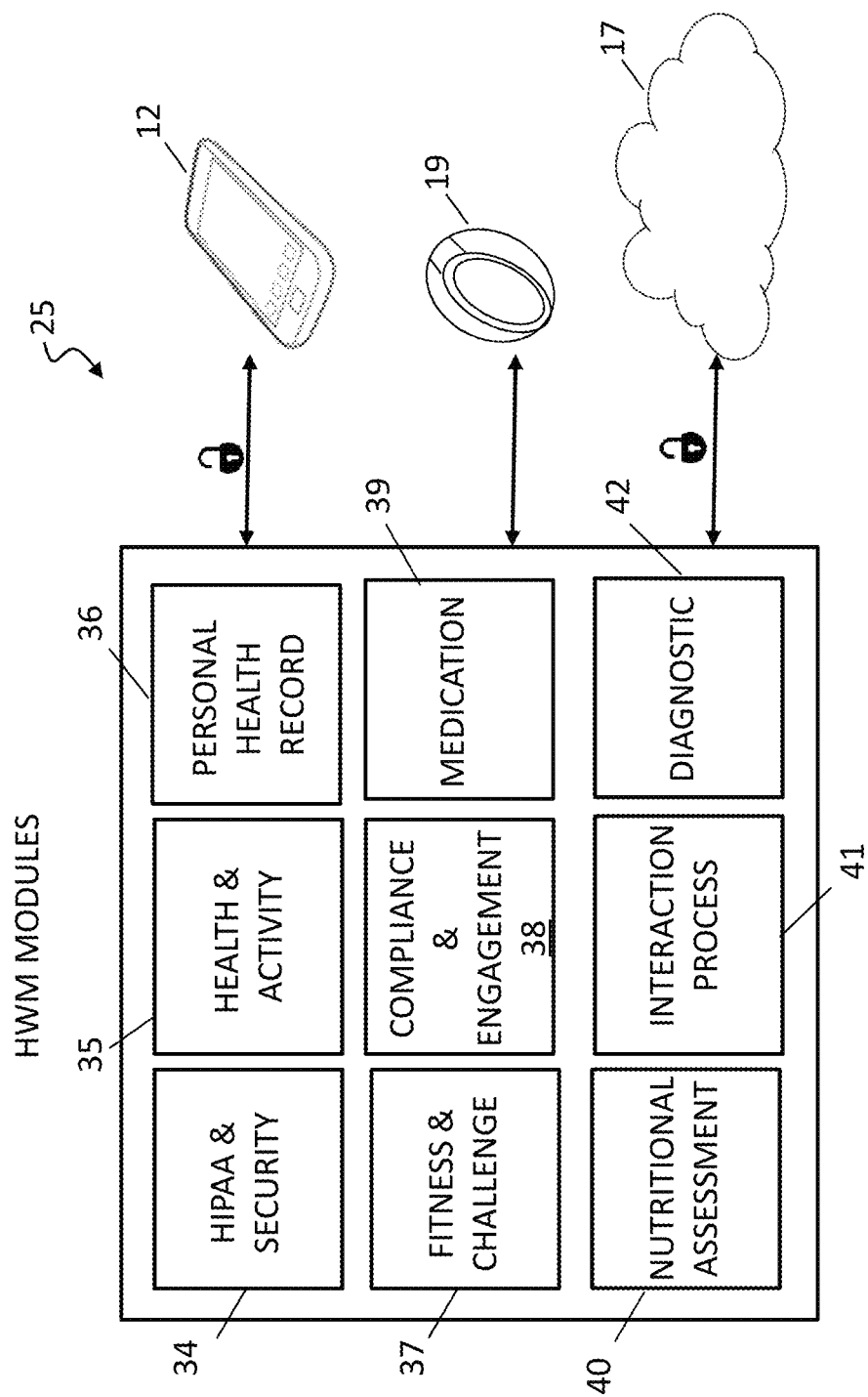
FIG. 3 is a simplified block diagram of exemplary health and wellness mobile management (HWM) modules of the health and wellness mobile management system and method according to an exemplary embodiment of the present disclosure.

FIG. 3 is a simplified block diagram of exemplary health and wellness mobile management (HWM) modules 14 of the health and wellness mobile management system and method according to an exemplary embodiment of the present disclosure. These HWM modules include HIPAA & security module 34, health & activity module 35, personal health record module 36, fitness & challenges module 37, compliance & engagement module 38, medication module 39, nutritional assessment module 40, interaction process module 41, and diagnostic module 42. These HWM modules may be embodied as apps executing on a mobile platform 12 (e.g., mobile telephone) as well as logical modules on a web browser-based application 20, such as a portal (here represented by a cloud). Any of these modules may be external third party modules that the system may interface and interact with using external connect interface 32 or other suitable means. These modules also communicate with a variety of external monitoring devices 19. Some of the HWM modules are described in more detail below.

The HIPAA & security module 34 ensures that there is no unauthorized access to data. This module 34 uses state of the art authentication methods to validate data access requests. The patient may easily set up data access permissions and terminate permissions. This module 34 also ensures that data is handled in compliance with HIPAA regulations. This module 34 is described in more detail below in conjunction with FIGS. 5 and 6.

The health & activity module 35 receives and analyzes the patient's physiological data to monitor the general health and activity status of the patient. The patient's data may be compared with general population thresholds or with thresholds set by the patient's physician. Behavioral modification techniques are employed to encourage the patient to self-monitor as well as get enough exercise for healthful benefits.

The personal health record module 36 provides an easy interface for the patient to review his/her own health data, and to view and generate reports analyses related to her health data. Described in more detail below, the patient's access may be automatically verified by the use of wearable patient ID.

The fitness & challenge module 37 provides a way to motivate users to reach certain fitness goals. This module 37 is described in more detail below in conjunction with FIG. 8.

The compliance & engagement module 38 tracks the patient's medicine and supplement intake and encourages compliance with the doctor's prescription and orders. This module 38 may use a variety of ways to monitor the patient's medicine and supplement intake, such as smart medicine and supplement containers, video feed, etc. This module 38 may present reminders to the patient at the appropriate time, and issue notifications to the physician for compliance and/or non-compliance. Behavioral modification techniques are employed to encourage the patient to adhere to the doctor's prescribed regimen.

The medication module 39 maintains data about the patient's current medicines, details about the medicines, medical history, compliance data, reminders, ineffective medicines for the patient, medical allergies, and side effects associated with any current and past medicines.

The nutritional assessment module 40 maintains data about the patient's nutritional intake and provides further analyses about the data. In particular, the patient may obtain a quantitative valuation of his/her nutritional intake on a per food item, per meal, per day, per week, per month, per quarter, and per year basis. This module 40 also provides the ability to further analyze the data, such as perform trend analysis, comparison between different time periods, etc. Behavioral modification techniques are employed to encourage the adoption of more healthful eating habits. This module 40 is described in more detail below in conjunction with FIG. 9.

The interaction process module 41 enables the patient to check drug prescriptions for possible interactions, as well as interactions with food and supplements. This module 41 automatically looks up the database for any known interactions between drugs, supplements, and food.

The diagnostic module 42 receives a patient's medical/health data, monitored physiological data, and self-reported data, and performs diagnostic analysis of the data. The diagnostic module 42 is able to preemptively provide diagnosis to the patient's physician to allow for early intervention before health issues arise. This module 42 thus enables the patient's healthcare provider to focus early on the patient's health issues before they arise, and to take preventative measures to achieve the best outcome. For example, the patient's blood pressure may be elevated for a period of time exceeding a general or custom threshold. This information is transmitted to the physician or healthcare provider, who may ask the patient to come in for an appointment to see if blood pressure medication is indicated. As another example, by monitoring and determining that the patient's body temperature has dropped below a certain threshold, the patient's hypothermic condition may be detected well in advance of any irreversible harm. As another example, the body temperature of a patient that is immunocompromised may be monitored to detect early signs of an infection.

The computing device 12 is further operable to communicate, preferably wirelessly, with a variety of external monitoring devices 19. The external monitoring devices 19 may be used for compliance and verification purposes. For example, an external monitoring device 19 may be a device that is operable to measure lung function (e.g., a spirometer) and carbon monoxide (CO) of a patient, which may be used to detect smoking cessation compliance. Numerous efforts have been attempted to curtail smoking, ranging from hypnosis, peer support groups, negative reinforcement, biofeedback, nicotine gum and patches, prescription medication, electronic cigarettes, and counseling. While some of these aids have been helpful, recidivism is high and thus early intervention when risky behavior is initially resumed would significantly improve the odds of quitting. Additionally, because many health and life insurance policies set the cost of premiums based on factors including cigarette smoking, the ability to confirm cessation compliance and thus qualify for risk-adjusted health premium is of importance. The combined spirometer and CO sensor, hereinafter referred to as home smoking cessation monitoring device, a type of external monitoring device 19, is operable to measure the volume of air as well as the CO content of inhaled and/or exhaled breath of a patient. Data from the first measurement can be used to determine pulmonary capacity and function (and indirectly oxygen saturation level), and data from the second measurement can be used to determine the amount of blood CO or CO poisoning in the patient. In a patient that has quit smoking, such monitoring should see improved lung capacity and decreasing CO poisoning. Acute changes in the CO level is an especially good assessment of cessation compliance as CO level will immediately rise if the patient smokes and remain elevated for 24-48 hours. Therefore, the home smoking cessation monitoring device can verify that the patient has continued with smoking cessation efforts. Compliance and engagement may elicit positive messaging and encouragement from the system.

The home smoking cessation monitoring device 19 may include a mouthpiece into which the patient would inhale and exhale. The handheld device includes microprocessor operable to execute software code performing logic and mathematical algorithms to compute quantities that assess the patient's lung function and blood CO content. The device may include a display screen that displays operating instructions, data quantities, and graphical output, for example. The display screen may be touch-sensitive to receive user input. The device may also include a data port such as a USB port and/or a wireless communication module including a transceiver, such as a Bluetooth communication module, to wirelessly communicate with the computing device 12. Therefore, the device may receive and convey data to and from the computing device 12. Other forms of suitable wireless communications technology and protocols can also be employed. The computing device 12 may receive the measurement data, perform analysis on the data, display the data in a desired manner, prepare reports incorporating the data, and log the measurement data, for example.

It is advantageous to combine both spirometry and CO measurement in one handheld device that is portable and can be easily used by the patient at home. The amount of time the patient spends in making measurements is significantly decreased as both parameters are measured simultaneously. The shortened time and wireless communication make the measurement process easy and convenient for the patient. The measurement data can also be easily associated with one particular individual and account and relayed to the health and wellness management system 10. Healthcare professionals may then easily monitor a patient's smoking cessation compliance via a tele-health platform such as system 10 described herein. The handheld device may further incorporate blood pressure and heart rate measurement functions, and additionally an oxygen sensor.

Smoking immediately increases the blood CO level, heart rate (pulse), and blood pressure with decreased and cumulative pulmonary changes. Measuring these parameters in a smoker may motivate them to quit smoking and reinforce cessation benefits as these measurable physiological changes are presented and displayed to the patient. Normal CO level measurements are used to verify smoking cessation compliance which may reduce healthcare insurance premiums. Further, monitoring a population may allow early detection of risky behavior and adaptation for early intervention. An estimated 43.8 million adults smoke cigarettes daily with a total cost in medical and productivity of $193 billion ($96 billion in health expenditures and $97 in productivity loss) or $4,406.39 per smoker. Cigarette smoking is the leading cause of preventable death in the United States and accounts for 440,000 deaths, or one in five. Although the number of adults who smoke has decreased over the last several decades from a peak of 45% of US adults in the mid 1950's, it is still a very costly and risky behavior. Of the over 7,000 chemicals found in tobacco smoke, at least 250 are known to be harmful and at least 69 are known carcinogens. The harmful effects of second hand smoke has also been documented. Therefore, increasing the success of smoking cessation significantly decreases the overall cost of healthcare and improves the health of the general population.

In addition to monitoring and documenting smoking cessation, the computing device 12 may be operable to communicate, preferably wirelessly, with other external monitoring devices adapted to measure physiological parameters, such as blood pressure, blood oxygen content, pulse rate, etc. The external monitoring device may be used to detect other forms of substance abuse. For example, the external monitoring devices may be used for monitoring blood alcohol content or the presence of illegal drugs and other substances.

Figure 4:
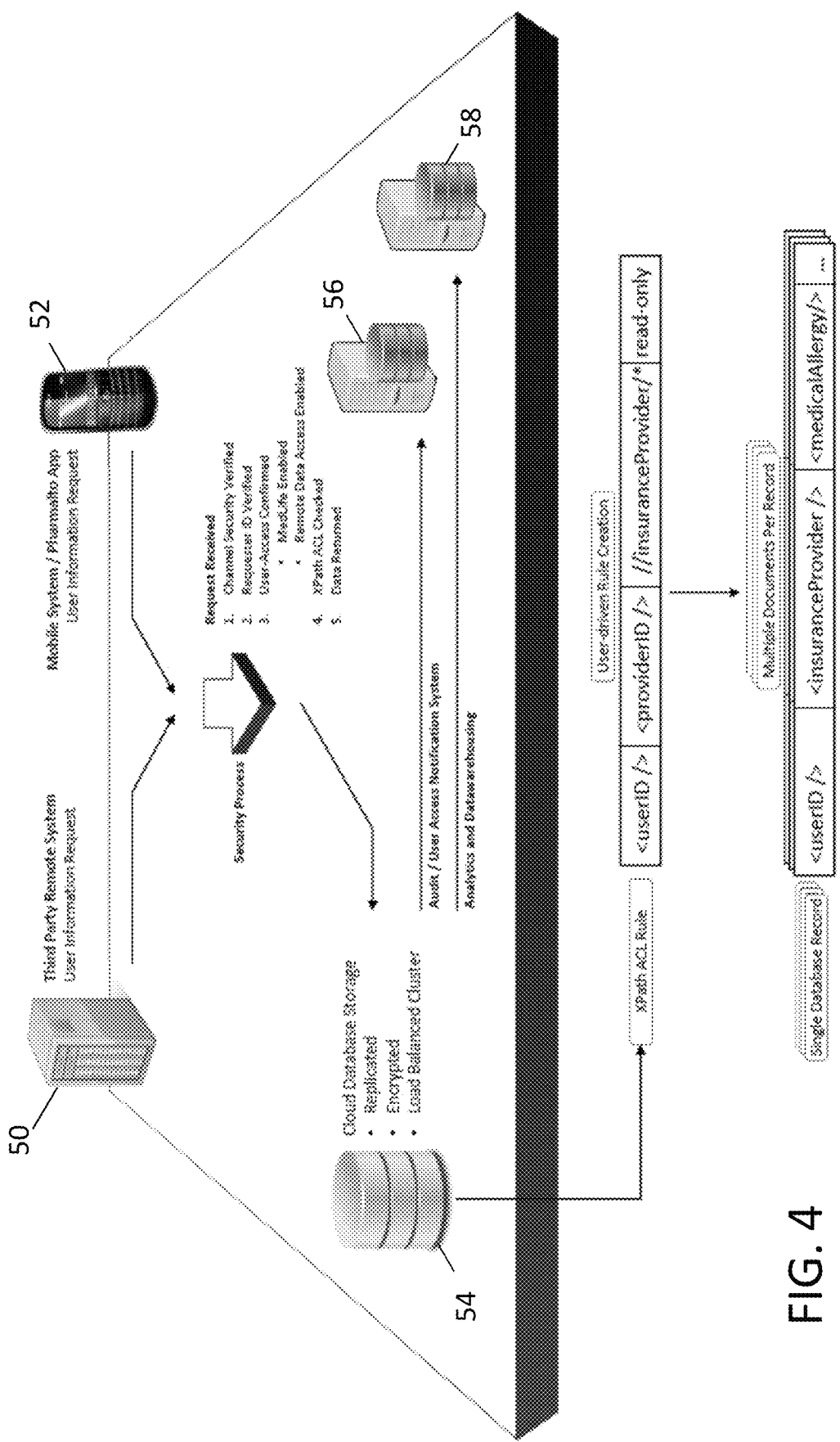
FIG. 4 is a simplified data flow diagram illustrating a process of user information request according to an exemplary embodiment of the present disclosure.

FIG. 4 is a simplified data flow diagram illustrating a process of user information request according to an exemplary embodiment of the present disclosure. User information requests may come from third party remote systems 50 or mobile computing devices executing the health and wellness management app 52, for example. All user information requests must be first screened to ensure proper authentication and verification. This process may include verifying communication channel security, verifying the requester's assigned ID, confirming that the owner of the data has enabled information requests, and verifying against the Access Control List (ACL) that the requester has authorization to access the data. The ACL may define one or more data access levels that define narrow to broad access permission to the data. The patient's data is stored in a cloud database 54, which employs conventional database technologies to provide, for example, redundancy, load balancing, and data encryption. The system 10 also includes an audit database 56 and an analytic database 58. The audit database may store record change logs, system logs, and other audit data that may be necessary to ensure HIPPA compliance, for example. The analytic database 58 warehouses data related to business intelligence and is optimized for data retrieval, aggregation, tabulation, dissemination, and analytics for business intelligence analysis purposes.

A patient's data may be organized as a single record that may consist of multiple documents. Each document and each record is identified with or linked to the patient's or user's identifier, userID. This userID is used to identify the owner of the data, which may be patient or a legal guardian of the patient, for example. In addition, The patient's insurance providers, medicine prescriptions, supplements, and other health and wellness data are stored according to predetermined schema in the multiple documents of the record. These multiple documents comprise the wholly-owned instance of medical record of the patient, and access by any other individual or entity has to be granted permission by the data owner (the patient and/or legal guardian).

Access Control Lists (ACL) or another suitable technique may be used to define and implement rules for users to allow or deny access to any or all parts of the documents in a record. ACL may be used to define roles and the access rights associated with the roles. XPATH expressions may be used to manage the ACL rules as known in the art.

FIG. 5 is a simplified flowchart illustrating a method of HIPAA and security setup process 60 according to an exemplary embodiment of the present disclosure. Initially, as shown in block 62, the data owner (patient) inputs authentication information that will be used to gain access to the health and wellness data. This may include the data owner's name, userID and/or other forms of unique identification (e.g., social security number, etc.), password, biometric data, machine-readable code, etc. The biometric data may include fingerprint(s), iris scans, facial recognition, and other forms of unique physical trait from the data owner. Machine-readable code may include digital and/or analog signals that can be generated by devices like RFID, near field communication (NFC), two-dimensional machine-readable code (e.g., QR or Quick Response code), etc. In block 64, the received user login or authentication information is preferably encrypted prior to storing it in the database. The user may also provide information about persons who have permission to access the data, as shown in block 66. The user may enter specific information about the permitted users along with their names and ID, methods of access, password, and what subsets of data is available to each permitted user. The login information is received and preferably encrypted prior to storage, as shown in block 68. The login information may be stored in cloud database along with the patient health and wellness data. The process terminates in block 70.

FIG. 6 is a simplified flowchart illustrating a method of HIPAA and security revocation/modification process 80 according to an exemplary embodiment of the present disclosure. The patient or data owner may login by entering his/her login information, as shown in block 82. The system and process verify the login information, as shown in block 84. The patient/data owner may then select a particular data access permission holder from a list of current users as someone whose permission he is now terminating, as shown in blocks 86 and 88. The system and method then updates information relating to current access permission holders, as shown in block 90, and the process terminates in block 92.

It should be noted that all of the data entry may be done at a web-based portal or by using an app running on a mobile device. Further, the patient/data owner may, at any time, accept or terminate an information sharing arrangement with a healthcare provider or institution, thus eliminating the need for HIPAA document exchange. It is preferable that the healthcare providers, organizations, and other entities who wish to gain access to the patient data become a registered provider or registered institution of the system.

Figure 7:
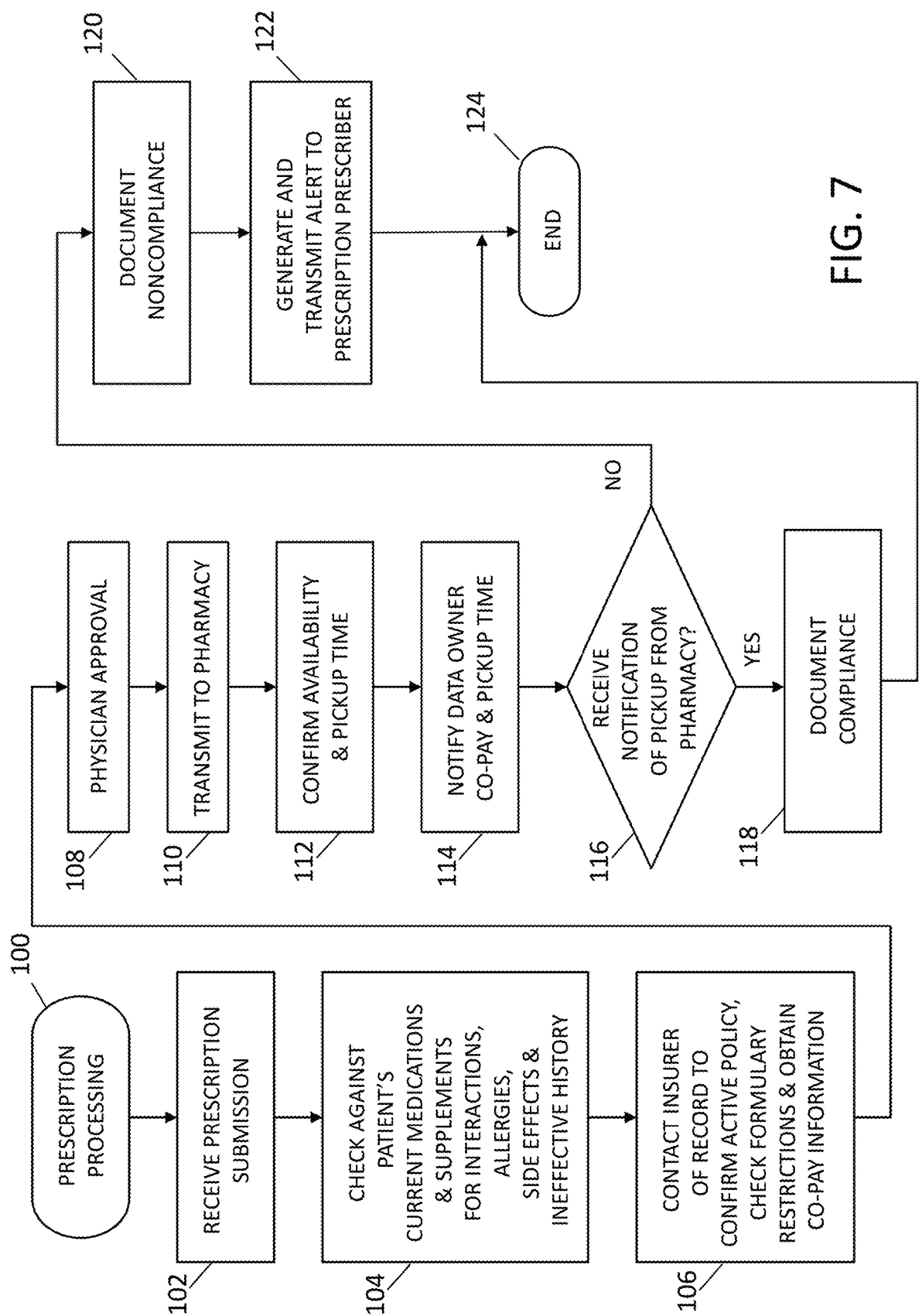
FIG. 7 is a simplified flowchart illustrating a method of electronic prescription processing according to an exemplary embodiment of the present disclosure.

FIG. 7 is a simplified flowchart illustrating a method of electronic prescription processing 100 according to an exemplary embodiment of the present disclosure. The system 10 receives an electronic prescription submitted by the physician, physician assistant, or another personnel at the physician's clinic or office 102. Prior to providing access to the system 10, the person submitting the prescription must log-in to the system via a web-enabled computing device executing a web client such as a browser. The system 10 may provide third parties such as physicians and pharmacies dedicated portals for accessing the patient data. After proper log-in, the personnel may enter all data related to the prescribed medication, including but not limited to, the medication name, whether a generic substitute is allowed, dosage, the manner in which the medication should be taken or applied, insurance provider information or selection, pharmacy selection, etc. After the prescription information has been submitted, preliminary verification that all necessary data fields have been filled in properly can also be made prior to proceeding further. It should be noted that some or much of the information does not need to be re-entered each time the prescription is refilled. A patient may have a chronic condition that requires the same medication, and the physician may just need to select the medication from a list of medications associated with the patient. The insurance provider, pharmacy information may also be stored in the system as well and just require confirmation when the physician is submitting the prescription.

In block 104, the received prescription submission is checked against the patient's current medications, supplements, and health history for possible interactions (with existing medications and supplements), allergies, side effects, and ineffective history. If any such conditions has been found, it is flagged for review, for example. This screening process helps to eliminate waste and improve the patient's compliance. The physician may select an alternate medication, adjust dosage, etc. in response to the flagged conditions. In block 106, the system 10 contacts the selected insurance provider to confirm that the policy is still active, and further checks for formulary restrictions, and obtain or confirm the co-pay information. Other verifications may also be performed.

Once these verifications have been performed, the physician is requested or alerted for final approval in block 108. This may be done with a push notification on the physician's own computing device that is recognized by the system 10 (by using cookies, IP address, or other mechanisms). Because the prescription submission and prescription approval may be done on different computing devices, an extra layer of security is achieved. After the physician signs off and approves the prescription, the prescription is electronically transmitted to the pharmacy in block 110. Alternatively, an e-prescription service may be used for some of the data verification steps and the interaction with the pharmacy.

In block 112, the system 10 confirms with the pharmacy the availability of the prescribed medication and a pick-up time. In block 114, the owner of the data or the patient is notified of the pick-up time for the medication via his/her computing device by text, email, or another form of communication. The patient may also be notified of the co-pay information. In block 116, the system 10 receives a notification from the pharmacy when the medication has been picked up by the patient. The system 10 may set a time limit as to when the medication should have been picked up, such as three days, for example. The system 10 may also send reminders to the patient if pick up has not occurred within a specific timeframe. Similarly, refill reminders may also be sent. If the medication is picked up within this pre-set time frame, then the system documents compliance in block 118. Otherwise, the non-compliance is documented and a notification is transmitted to the physician that prescribed the medication in blocks 120 and 122. The process ends in block 124. Because prescription non-compliance is a $290 billion problem, the system 10 makes note of any non-compliance and notifies the appropriate individuals or entities when non-compliance is detected. This module incorporates behavioral modification techniques using authoritative, peer, and cause and effect methods to encourage compliance.

The system 10 may also employ video capabilities of the computing device to document compliance. The patient may be asked to turn on the video function of the device and record himself/herself when the medication is taken. These videos are recorded and compliance is logged for monitoring. Compliance is especially important for the treatment of certain medical conditions, such as inconsistent and incomplete treatment associated with rising drug resistant strains of tuberculosis.

Other types of data may be entered into the system following a similar procedure. The data are entered via a web interface, preferably mobile web interface, and data verification is performed on the fly or after the data are submitted. Suitable notifications or reminders are set according to the type of data entered. Similarly, suitable notifications may be transmitted to individuals or entities depending on the type of data.

Figure 8:
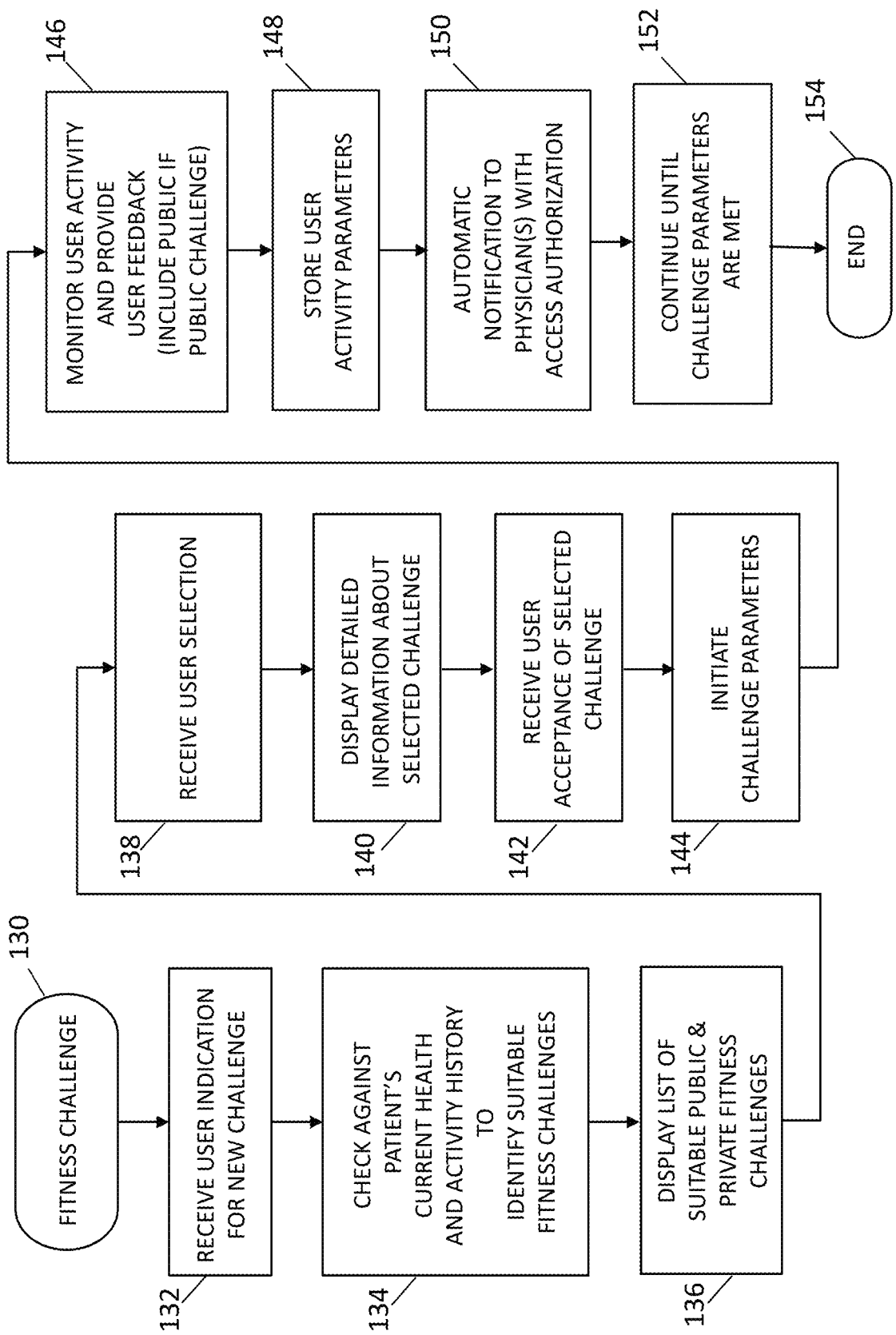
FIG. 8 is a simplified flowchart illustrating a method of fitness challenge process according to an exemplary embodiment of the present disclosure.

FIG. 8 is a simplified flowchart illustrating a method of fitness challenge process 130 according to an exemplary embodiment of the present disclosure. In block 132, the system 10 receives, via a mobile app or web-based application, an indication from the user to enter into a new fitness challenge. A fitness challenge is a public or private activity that has well-defined parameters. The fitness challenges may be designed by fitness experts or designed by the patient. For example, a bucket list item for this patient may be to walk the length of the Appalachian Trail. So the patient may add a fitness challenge that includes the parameters, i.e., length, elevation change, etc., of the trail, and set a time limit for completion. For example, fitness challenges may be in the form of running 20 miles each week for three months, walking the length of the Appalachian Trail within a certain time period, swimming the distance from Key West to Cuba within a certain time period, and climbing the height of Mt. McKinley within a certain time period. The more advanced challenges may be broken up into multiple parts or goals that are more easily achieved. A public or group challenge is one that have multiple participants that start at approximately the same time, and where the participants are given communication channels among them so that individuals' progress is posted and known to others within the group. Public or group challenges are carried out in a social manner so that peer pressure and encouragement from other participants in the group help motivate continued engagement and achieving the ultimate goal. The user may choose members of the group or allow the system to put together all individuals that are interested in the same fitness challenge. Thus, peer support and encouragement is employed to help the user adhere to the challenge and adopt a more healthful behavior.

The individual participant's progress may be self-reported and/or monitored by using activity or fitness trackers such as FITBIT, JAWBONE, APPLE watch, MISFIT, MOOV, and other comparable wearable devices. Initially, the system 10 checks the patient's health, wellness, and activity history to determine suitable fitness challenges to recommend to the patient, as shown in block 134. The patient's physician may also take part in or be consulted in pre-selecting best suited fitness challenges for the patient. The system then displays or otherwise presents to the patient a list of suitable private and public fitness challenges, as shown in block 136. The user makes his/her selection, which is received by the system, as shown in block 138. The system displays or presents more detailed information about the selected challenge, as shown in block 140. The user may then indicate his/her an acceptance of the selected private or public fitness challenge, as shown in block 142. The system then initiates the monitored parameters for the selected fitness challenge, as shown in block 144. For example, if the user decides to take on the fitness challenge of running 20 miles each week for three months, then the fitness parameters that are initiated may include start date, end date, mileage for each day of the challenge, accumulated mileage for each week of the fitness challenge, health parameters (e.g., pulse rate, body temperature, blood pressure, calories burned, weight, and BMI (body weight index)) for each day of the fitness challenge, environmental measurements (e.g., ambient temperature, humidity, elevation) etc.

When the user begins the fitness activity for a challenge, the fitness parameters are measured and monitored, as shown in block 146. When appropriate, the user is provided audio and/or visual feedback of selected fitness parameters as well as analysis of these monitored parameters. For example, the system may convey to the user that his pulse rate is too rapid for the exercise level, that his body temperature is too high, that he should hydrate given his activity level, that X miles from the first goal, and that he is ahead of others in the group in a public challenge, and the number of calories burned. All of the measured and monitored fitness parameters are stored in the system database(s), as shown in block 148. The current data feedback as well as stored historic data may be reviewed by the patient especially for correlation with positive outcomes in prescribed treatment, health regimen, exercise routine, healthful diet, etc. to further encourage compliance and engagement that lead to better outcomes. This historic data is also available for trend and other types of analyses. Further, automatic notification or reporting of all of selected fitness parameters may be transmitted to one or more authorized people such as the patient's physician(s), as shown in block 150. The patient's activities with respect to the fitness challenge are monitored and recorded continually, until the challenge is met, as shown in block 152. The process ends in block 154.

Figure 9:
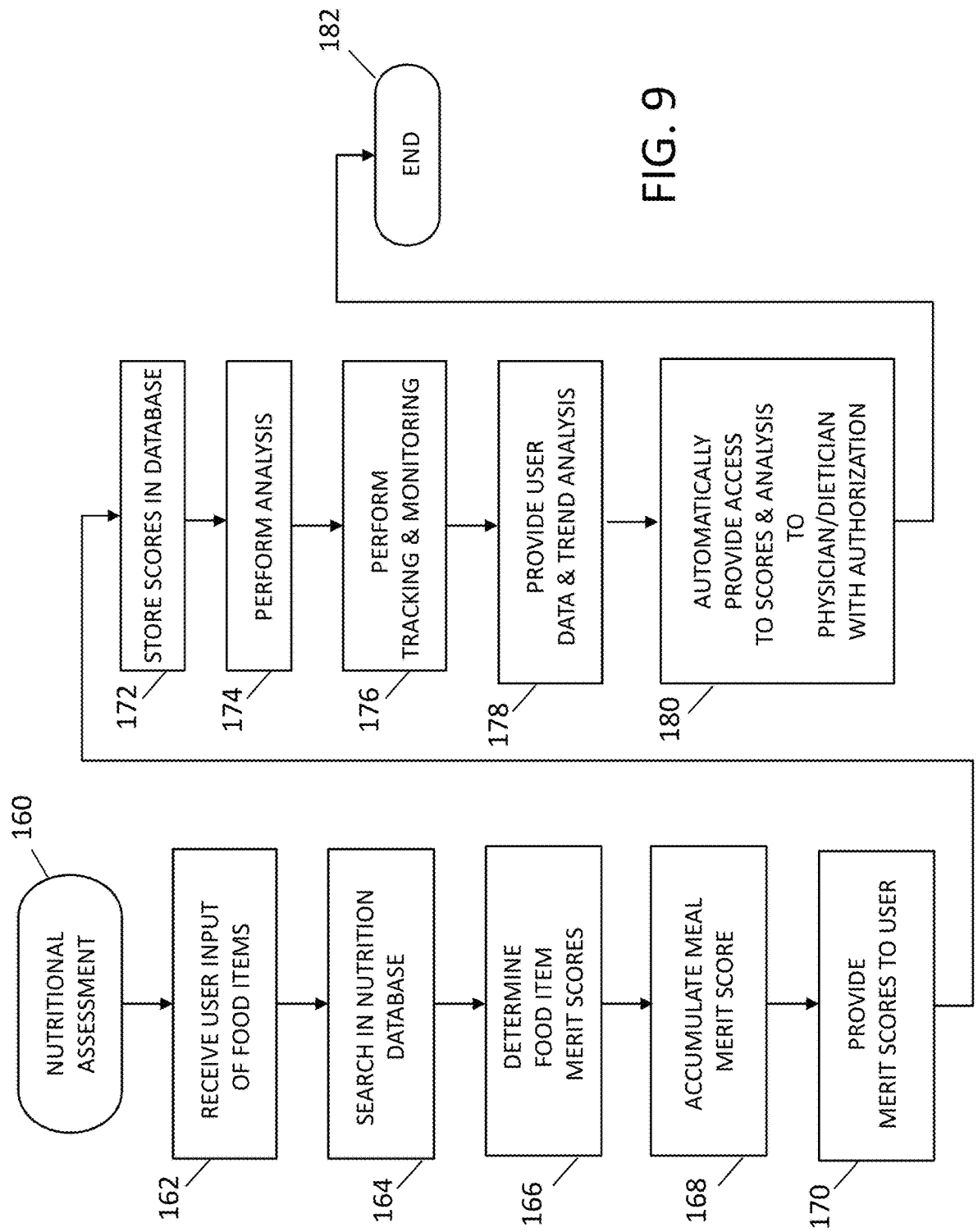
FIG. 9 is a simplified flowchart illustrating a method of nutritional assessment process according to an exemplary embodiment of the present disclosure.

FIG. 9 is a simplified flowchart illustrating a method of nutritional assessment process 160 according to an exemplary embodiment of the present disclosure. The system 10 may receive user input of food items, as shown in block 162. The manner of input may include, text entry, verbal input, taking a picture of the food item, taking a scan of a machine-readable code (e.g., barcode or QR code), and other methods now known or to be developed. For example, if the user intends to consume an orange, the user can take a picture of an orange or scan the barcode label affixed by fruit producers or grocer. The system analyzes the text entry, verbal input, picture, or machine-readable code, and identifies the food item by consulting a nutrition database, as shown in block 164. Upon locating the food item in the nutrition database, the system may look up a merit score for the food item, as shown in block 166. These scores are determined based on many properties of the food, such as calories, amount of fiber, amount of protein, amount of sugar, quantity, the type of food (meat, carbohydrate, fruit, vegetable, etc.), how it's prepared (e.g., raw, steamed, fried, sautéed, and broiled), that has been calculated by professionals after detailed analysis as to how good or beneficial particular food items are for human health and wellness, and specifically for this patient given his health condition and medical issues (current, genetic, and predicted). Further consideration may also be given to beneficial or harmful effects of when certain foods are eaten together. If the user is consuming more than one type of food item, then the same process is repeated to enter each food item. For example, if the user's meal includes a piece of baked cod fish, broccoli florets, and carrots, each food item may be entered consecutively. Alternatively, the system has sufficient artificial intelligence to analyze a photograph to identify each type of food item arranged on a plate, for example. The system is able to assign a food merit score for each item and present to the user individual scores for each type of food item, as well as an accumulated or total score for the entire meal, as shown in blocks 168 and 170. The food merit scores are then stored in the patient's database records, as shown in block 172. The current feedback and availability of historic data are especially beneficial for correlation with positive outcomes to further encourage compliance and engagement, which leads to better outcomes. Such behavioral modification techniques are employed to encourage the development of more healthful eating habits. Analysis may be automatically performed and the results presented to the user, as shown in block 174. Further, tracking, monitoring, and trend analysis may also be performed and the results presented to the user, as shown in blocks 176 and 178. The food merit score and analysis data may also be automatically transmitted to one or more authorized persons, such as a physician or dietician, as shown in block 180. The process ends in block 182.

It should be noted that the patient may also choose to accept a private or public nutrition challenge that is conducted similar to the fitness challenge described above. In a nutrition challenge, the user may choose to eat food that has a food merit score of X or higher for a month, for example.

Figure 11:
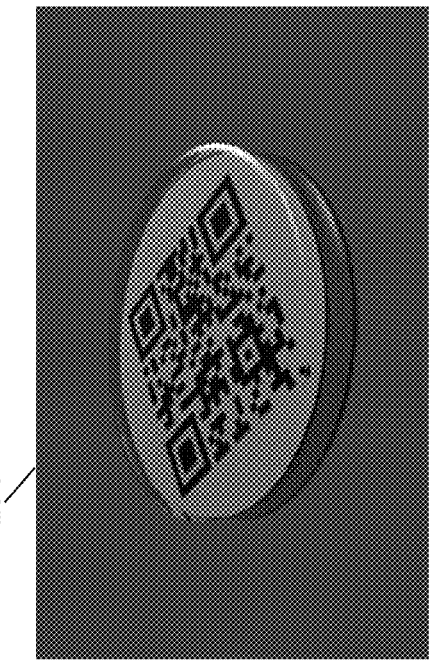
FIG. 10-12 are exemplary views of an ID button that may be incorporated in a variety of accessories to identify a health and wellness mobile management service subscriber according to an exemplary embodiment of the present disclosure.
Figure 10:
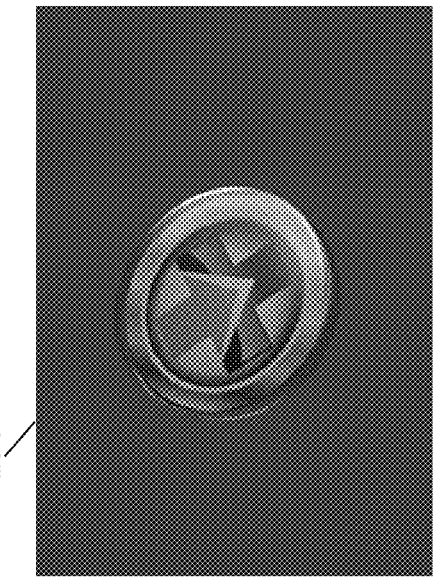
Figure 12:
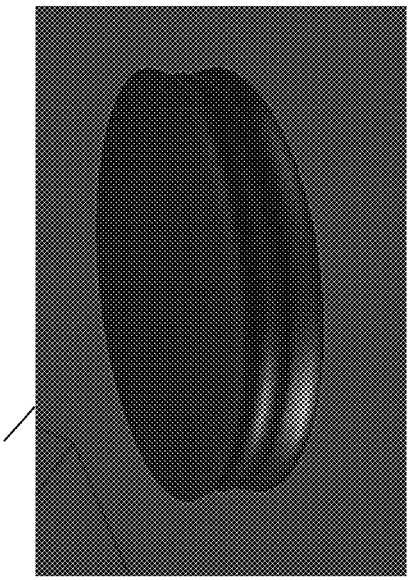

Access to a patient's data may be granted by the patient or data owner. Additionally, access may be granted via automatic recognition of the patient/data owner, such as using biometric data (fingerprints, facial recognition, retina recognition, etc.), near field communication (NFC), or one-dimensional or two-dimensional machine-readable code. FIG. 10-12 are exemplary views of an ID button 80 that may be incorporated in a variety of accessories to identify a health and wellness mobile management service subscriber or user according to an exemplary embodiment of the present disclosure. An exemplary embodiment is an acrylic coated button with a logo identifying the health and wellness mobile management system on one side, and a two-dimensional bar code or QR (Quick Response) code on the second side. Alternatively, RFID (radio frequency identification) technology may be incorporated into the ID button 190. Scanning the code with a code reader application incorporated in a computing device redirects the app to the system website. The patient/data owner may enable this type of data access by emergency medical personnel, and pre-set the type of information that may be accessible to someone who accesses the system 10 using the ID button. For example, the user may specify that emergency medical information is viewable by a third party (e.g., an EMT) redirected by the button ID, for example. The emergency medical information may include name, age, gender, an emergency contact name and phone number, medical conditions such as diabetes, heart issues, hypertension, etc., medications, supplements, allergies or sensitivities, past surgeries, etc.

An emergency medical personnel who has pre-registered to be able to access the health and wellness data in the system 10, and in particular the specific patient/data owner's data can use a pre-assigned code, for example, to gain authorization to access the emergency medical information. When such user attempts to gain access to the data, by using scanning the ID button, for example, the patient/data owner is notified or alerted. Such attempts and subsequent access of the data are logged for audit and reporting purposes. The scanning of the code on the ID button may automatically provide the emergency personnel an emergency contact for the patient/data owner.

Figure 14:
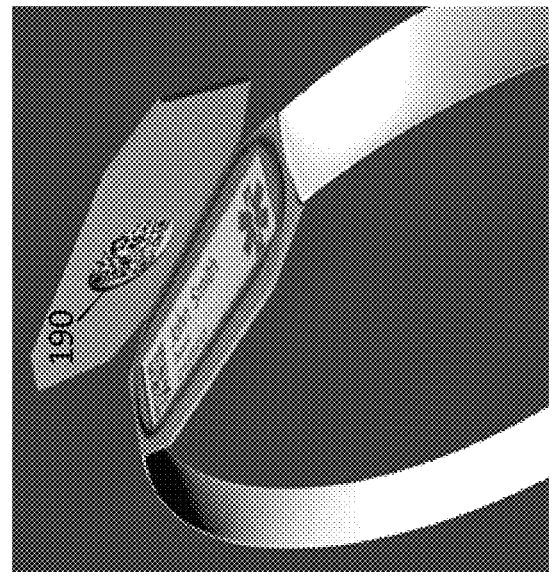
FIGS. 13 and 14 are exemplary views of the ID button incorporated into a bracelet according to an exemplary embodiment of the present disclosure.
Figure 13:
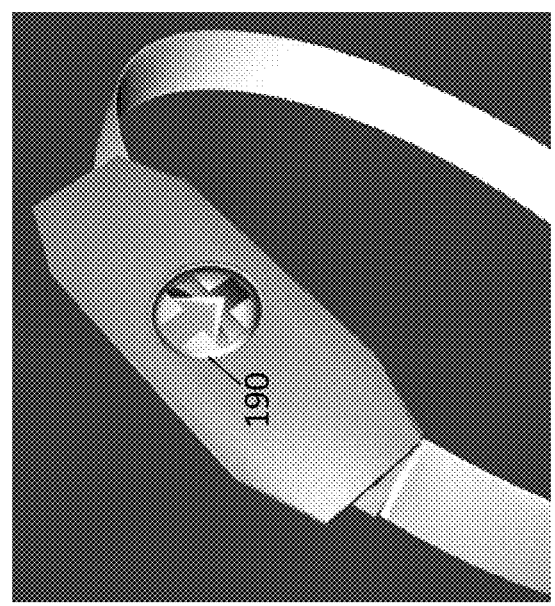

FIGS. 13 and 14 are exemplary views of the ID button 190 incorporated into a bracelet according to an exemplary embodiment of the present disclosure. The button ID may be incorporated into a number of other accessories, such as luggage tag, key chain, medical wrist band, necklace, ring, etc. In the event of an emergency, emergency medical technicians may easily recognize a patient who is a subscriber of the health and wellness mobile management system, and can easily access medical information that may be critical to address the emergency at hand. The ID button may be incorporated as part of an overall authentication process, which may require the presence of the ID button as well as another form of identification, such as biometric, password, etc.

The features of the present invention which are believed to be novel are set forth below with particularity in the appended claims. However, modifications, variations, and changes to the exemplary embodiments described above will be apparent to those skilled in the art, and the system and method described herein thus encompass such modifications, variations, and changes and are not limited to the specific embodiments described herein.

What is claimed is:

1. A health and wellness mobile management system independent of a healthcare entity and soley owned and controlled by a patient, comprising:

a database operable to store a health and wellness data record associated with a patient who is the sole owner of the data and has sole control over access authorization and storage of the data, the health and wellness data selected from the group consisting of medicines, supplements, medical history, compliance data, reminders, ineffective medicine, side effects, healthcare provider data, pharmacies, allergies, vaccination record, lifestyle data, exercise data, dietary data, legal documents, medical charts, laboratory data, imaging data, emergency contact data, and insurance data;

a data management system adapted to strictly control access to the health and wellness data record stored in the database according to access rules and authorization solely set by the patient;

a web interface adapted to interface with information requesters submitting requests for entering and accessing the health and wellness data record via a web application executable by a computing device selected from the group consisting of mobile telephones, mobile gaming devices, tablet computers, laptop computers, and desktop computers, the information requesters submitting identification information and authorization soley granted by the patient;

the web interface further configured to receive patient's self-reported data to update the data in the health and wellness data record;

an external connect interface adapted to interface electronically with external systems and applications associated with at least one of physical therapists, emergency medical technicians, healthcare providers, pharmacies, hospitals, emergency rooms, acute care facilities, laboratories, outpatient surgery centers, benefits manager and insurer content management systems, and to interface with at least one third party live data monitoring and analysis systems for receiving health and wellness data associated with the patient for storing in the health and wellness data record in the database;

a prescription interface in communication with the database adapted to receive a pharmaceutical prescription for a prescribed medication for the patient submitted by a healthcare provider, verify the submitted pharmaceutical prescription against data in the patient's health and wellness data record, request and receive approval for the submitted pharmaceutical prescription, and monitor patient compliance including receiving the prescribed medication and following instructions in using the prescribed medication; and an automatic identification device worn by the patient adapted to automatically wirelessly, and uniquely identify the patient as the data owner of the health and wellness data record stored in the database and to automatically grant access to the data, the identification device operable to automatically and wirelessly direct the web application to access a data subset of the health and wellness data record stored in the database upon recognition of access being granted.

2. The system of claim 1, further comprising:
an audit database storing audit-related data; and
an analytic database storing analytics-related data.

3. The system of claim 1, wherein the health and wellness data record comprise data in XML format.

4. The system of claim 1, wherein the access rules are specified by an access control list.

5. The system of claim 1, wherein the web application may be executed by a computing device selected from the group consisting of mobile telephones, mobile gaming devices, tablet computers, laptop computers, and desktop computers.

6. The system of claim 1, wherein the patient identification device comprises an accessory bearing machine-readable code identifying the patient.

7. The system of claim 1, wherein the patient identification device comprises an accessory bearing a two-dimensional machine-readable code identifying the patient.

8. The system of claim 1, wherein the patient identification device comprises an accessory bearing RFID identifying the patient.

9. The system of claim 1, wherein the patient identification device comprises a biometric characteristic reader.

10. The system of claim 1, wherein the patient identification device comprises an NFC device.

11. The system of claim 1, wherein the web interface is adapted to automatically notify a healthcare professional when certain patient health data exceed thresholds.

12. The system of claim 11, wherein the web interface is adapted to receive setting of health data thresholds from the healthcare professional.

13. The system of claim 1, wherein the web interface is adapted to transmit a notification to a healthcare professional when a certain monitored patient condition requires attention.

14. The system of claim 1, further comprising a physiological parameter measurement device adapted to automatically and wirelessly communicate with the external connect interface and operable to measure a physiological parameter of the patient, transmit the physiological parameter measurement.

15. The system of claim 14, wherein the physiological parameter measurement device is operable to measure at least one of heart rate, blood pressure, perspiration, carbon oxide content, and oxygen content.

16. The system of claim 1, wherein the identification device is further adapted to automatically and wirelessly communicate with the external connect interface and operable to measure a physiological parameter of the patient, transmit the physiological parameter measurement.

17. The system of claim 16, wherein the identification device is operable to measure at least one of heart rate, blood pressure, perspiration, carbon oxide content, and oxygen content.

18. The system of claim 1, wherein the identification device is adapted to automatically and uniquely identify another wearer of the identification device as having authorized access to the health and wellness data record stored in the database and to grant and provide the wearer access to the health and wellness data record stored in the database.

19. The system of claim 1, further comprising a nutritional value module adapted to:
receive data concerning a food item;
identify the food item in response to the received data;
determine a nutritional score for the identified food item in response to the patient's current and predicted health conditions; and
accumulate a total nutritional score for the patient's daily consumption and store the total nutritional score in the database.

20. A method for health and wellness mobile management, comprising:
providing strictly-controlled access to a database operable to store a health and wellness data record associated with a patient who is the sole owner of the data in the data record and has sole control over access authorization and storage of the data, the health and wellness data selected from the group consisting of medicines, supplements, medical history, compliance data, reminders, ineffective medicine, side effects, healthcare provider data, pharmacies, allergies, vaccination record, lifestyle data, exercise data, dietary data, legal documents, medical charts, laboratory data, imaging data, emergency contact data, and insurance data, the access to the health and wellness data record according to access rules set by the patient;
interfacing with information requesters including the patient submitting requests for entering, updating, and accessing the health and wellness data record via a web application executable on a mobile device, the information requesters submitting identification information and authorization granted by the patient;
interfacing electronically with external systems and applications associated with at least one of physical therapists, emergency medical technicians, healthcare providers, pharmacies, hospitals, emergency rooms, acute care facilities, laboratories, outpatient surgery centers, benefits manager and insurer content management systems, and third party live data analysis systems for receiving health and wellness data including self-monitoring activity data associated with the patient for storing in the health and wellness data record in the database;
further interfacing electronically with a personal health monitoring device for receiving additional health and wellness data associated with the patient for storing in the health and wellness data record in the database;
receiving, by a prescription interface, a pharmaceutical prescription for a prescribed medication for the patient submitted by a healthcare provider, verifying the submitted pharmaceutical prescription against data in the patient's health and wellness data record, requesting and receiving approval for the submitted pharmaceutical prescription, and monitoring patient compliance including receiving the prescribed medication and following instructions in using the prescribed medication;
automatically and wirelessly receiving a patient identifier uniquely identifying the patient as the data owner of the health and wellness data record stored in the database, the patient identifier operable to automatically direct the web application to access at least a data subset of the health and wellness data record stored in the database upon recognition of access being granted, and to enable entry of data by the patient via the web application.

21. The method of claim 20, comprising:
receiving an information request from an information requester;
verifying channel security of the information request;
verifying requester identifier;
confirming authorization for information requester to access the health and wellness data record;
confirming remote access to the health and wellness data record is authorized;
verifying the access rules; and
transmitting requested data to the information requester.

22. The method of claim 20, comprising receiving an information request from an information requester, wherein the information request comprises a machine-readable code identifying the patient and data owner of the health and wellness data record.

23. The method of claim 20, comprising receiving an information request from an information requester, wherein the information request comprises a two-dimensional machine-readable code identifying the patient and data owner of the health and wellness data record.

24. The method of claim 20, comprising receiving an information request from an information requester, wherein the information request comprises a RFID identifying the patient and data owner of the health and wellness data record.

25. The method of claim 20, comprising specifying the access rules by an access control list.

26. The method of claim 20, comprising receiving an information request from an information requester via the web application executing on a computing device selected from the group consisting of mobile telephones, gaming devices, tablet computers, laptop computers, and desktop computers.

27. The method of claim 20, further comprising automatically transmitting a reminder to the patient for picking up a prescription.

28. The method of claim 20, further comprising automatically transmitting a notification to the healthcare provider in response to patient medication and supplement non-compliance.

29. The method of claim 20, further comprising automatically transmitting a notification to the healthcare provider in response to a patient health data requiring attention.

30. The method of claim 20, further comprising automatically transmitting a notification to the healthcare provider in response to a patient health data exceeding a threshold set by the healthcare provider.

31. The method of claim 20, further comprising automatically checking the pharmaceutical prescription against the patient's health and wellness data for adverse conditions that may result.

32. The method of claim 20, further comprising videoing the patient to document and monitor compliance.

33. The method of claim 20, further comprising automatically transferring ownership of the health and wellness data associated with a minor upon reaching adulthood.

34. The method of claim 20, further comprising:
setting a general population threshold for a certain health parameter; and
monitoring for patient self-monitoring activities to screen for the certain health parameter exceeding the general population threshold.

35. The method of claim 20, further comprising:
setting a personalized threshold for a certain health parameter;
monitoring for patient self-monitoring activities to screen for the certain health parameter exceeding the personalized threshold; and
analyzing the self-monitoring activity data for disease and condition diagnosis.

36. The method of claim 20, further comprising automatically and wirelessly communicate with the external connect interface and operable to measure a physiological parameter of the patient, transmit the physiological parameter measurement.

37. The method of claim 20, further comprising measuring at least one of heart rate, blood pressure, perspiration, carbon oxide content, and oxygen content.

38. The method of claim 20, further comprising automatically and wirelessly communicating with the external connect interface and measuring a physiological parameter of the patient, transmit the physiological parameter measurement.

39. The method of claim 38, further comprising measuring at least one of heart rate, blood pressure, perspiration, carbon oxide content, and oxygen content.

40. The method of claim 20, further comprising automatically and uniquely identifying another wearer of the identification device as having authorized access to the health and wellness data record stored in the database and to grant and provide the wearer access to the health and wellness data record stored in the database.

41. The method of claim 20, further comprising enabling the patient to select a public fitness challenge in which a group of peers undertake the same fitness challenge and enabling communication among the patient and the group of peers.

42. The method of claim 20, further comprising enabling the patient to select and undertake a private fitness challenge.

43. The method of claim 20, further comprising:
receiving data concerning a food item;
identifying the food item in response to the received data;
determining a nutritional score for the identified food item in response to the patient's current and predicted health conditions; and
accumulating a total nutritional score for the patient's daily consumption and store the total nutritional score in the database.

44. The method of claim 43, wherein receiving data concerning a food item comprises receiving at least one of a text input, an image, au audio input, and machine-readable code.

45. A system for health and wellness mobile management, comprising:
a database operable to store a health and wellness data record associated with a patient/data owner, the health and wellness data selected from the group consisting of medicines, supplements, medical history, compliance data, reminders, ineffective medicine, side effects, healthcare provider data, pharmacies, allergies, vaccination record, lifestyle data, exercise data, dietary data, legal documents, medical charts, laboratory data, imaging data, emergency contact data, and insurance data;
a content management system adapted to strictly control access to the health and wellness data record stored in the database according to access rules set by the patient/data owner;
a web interface adapted to interface with information requesters submitting requests for access to, enter, and edit the health and wellness data record via a web application, the information requesters submitting identification information and authorization granted by the patient/data owner, the web interface further configured to receive the patient's self-reported data to update the data in the health and wellness data record;

an external connect interface adapted to electronically interface with external systems and applications for receiving health and wellness data associated with the patient for storing in the database;

the external connect interface further configured to interface automatically and electronically with a personal health monitoring device for receiving additional health and wellness data associated with the patient for storing in the health and wellness data record in the database; and a machine-readable patient identifier device adapted to wirelessly and uniquely identify the patient as the data owner of the health and wellness data record stored in the database, the patient identifier device being operable to automatically direct the web application to enable authorized access, data entry, and edit of the data in the health and wellness data record stored in the database, the patient identifier device further operable to automatically measure a physiological parameter of the patient including pulse rate and blood pressure, and transmit the physiological parameter measurement.

46. The system of claim 45, wherein the machine-readable patient identifier device comprises:

a mouthpiece adapted to enable a patient to inhale and exhale air into the device;

a logic module adapted to measure and determine a volume of the inhale and exhaled air, and a carbon monoxide content in the exhaled air;

a display screen adapted to display data associated with the measured volume of air in the inhale and exhaled air, and carbon monoxide content in the exhaled air; and a wireless transceiver operable to communicate with a mobile computing device and to transmit the measured volume of air in the inhale and exhaled air, and carbon monoxide content in the exhaled air.

* * * * *